(12) United States Patent
Hoshino et al.

(10) Patent No.: US 6,596,720 B1
(45) Date of Patent: Jul. 22, 2003

(54) ANTI-HIV COMPOSITIONS

(75) Inventors: Hiroo Hoshino, Maebashi (JP); Kenji Kitazato, Tokushima (JP); Masakazu Fukushima, Hanno (JP)

(73) Assignee: Taiho Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 10/111,396

(22) PCT Filed: Nov. 1, 2000

(86) PCT No.: PCT/JP00/07676

§ 371 (c)(1),
(2), (4) Date: May 3, 2002

(87) PCT Pub. No.: WO01/34162

PCT Pub. Date: May 17, 2001

(30) Foreign Application Priority Data

Nov. 5, 1999 (JP) ............................................ 11-315670

(51) Int. Cl.⁷ ............................................. A61K 31/535
(52) U.S. Cl. .................................................... 514/235.8
(58) Field of Search ...................................... 514/235.8

(56) References Cited

U.S. PATENT DOCUMENTS 5,380,727 A * 1/1995 Deziel et al. .......... 514/263.31
5,552,384 A * 9/1996 Deziel et al. ................. 514/17
6,294,535 B1 * 9/2001 Yano et al. .............. 514/235.8

* cited by examiner

Primary Examiner—James H Reamer
(74) Attorney, Agent, or Firm—Rothwell, Figg, Ernst & Manbeck

(57) ABSTRACT

The present invention provides:

an anti-HIV composition comprising at least one member selected from the group consisting of trifluridine and derivatives thereof, and a pharmaceutically acceptable carrier;

an anti-HIV composition comprising (a) at least one member selected from the group consisting of trifluridine and derivatives thereof, (b) a thymidine phosphorylase inhibitor, and a pharmaceutically acceptable carrier; and a composition for potentiating the anti-HIV activity of trifluridine and derivatives thereof, comprising a thymidine phosphorylase inhibitor and a pharmaceutically acceptable carrier.

21 Claims, No Drawings

ANTI-HIV COMPOSITIONS

TECHNICAL FIELD

The present invention relates to a novel anti-HIV composition.

BACKGROUND ART

In 1981, acquired immunodeficiency syndrome (AIDS) was recognized as a disease that greatly damages the human immune system and leads to patient death in many cases. Since then, more than 40 million people have been infected with the human immunodeficiency virus (HIV), and around 12 million people have died of AIDS. In 1997, about 6 million people became infected with HIV and about 2.3 million people, including 460,000 children died of AIDS (J. M. Mann et al., Scientific American Jul. 82, 1998).

In 1985, a synthetic 3'-deoxynucleoside, 3'-azide-3'-deoxythymidine (AZT), was reported effective in inhibiting HIV infection. Since then, other compounds such as 2',3'-dideoxyinosine (ddI), 2',3'-dideoxycytidine (ddC), 3'-fluoro-3'-deoxythymidine (FLT) and 2',3'-dideoxy-2',3'-didehydrothymidine (d4T) have been proven effective as anti-HIV drugs.

However, these anti-HIV drugs have many defects. For example, anti-HIV drugs such as AZT have serious toxicity which limits the amount which can be clinically administered. Therefore, sometimes the drugs can not be administered to patients, or even if they can be used, often their administration must be stopped in many patients. In addition, drug-resistant viral strains tend to develop quickly during monotherapy with such anti-HIV drugs and there is also cross-resistance, for example, between AZT and d4T and between AZT and ddC. Moreover, patients tend to develop various complications, concomitantly with AIDS.

Trifluridine is a compound first synthesized by Heiderberger et al. (Journal of American Chemical Society, vol. 84, 3597(1962)), and known to have potent antitumor activity in vitro (Cancer Research, vol. 28, 2529(1968)). It is also known that this compound has potent antiviral activity against herpes simplex virus and vaccinia virus, which are DNA viruses (Science, vol. 145, 585(1964), Pergamon Press, New York 1990, 1182–1201).

However, trifluridine is known to be rapidly decomposed and inactivated by thymidine phosphorylase in the liver, intestinum tenue, etc. (Cancer Research, vol. 32, 247(1972); Japanese Journal of Cancer and Chemotherapy, vol. 8, 262(1981) and vol. 8, 1548(1981)). In clinical trials, trifluridine showed unsatisfactory antitumor effects (Cancer Chemotherapy Report, vol. 55, 205(1971)).

Currently approved medical use of trifluridine is limited to an ophthalmic preparation for herpes keratitis caused by herpes simplex virus (HSV) infection, which is an ophthalmic local treatment and thus free from decomposition by thymidine phosphorylase (The Lancet, vol. 21, 1189(1987); Physicians Desk Reference, 50th Ed. 1204(1996); American Journal of Ophthalmology, vol. 73, 932 (1972); Journal of Acquired Immune Deficiency Syndromes and Human Retrovirology, vol. 12, 147(1996)).

Until now it has been completely unknown that trifluridine is useful for treating HIV infection, the cause of AIDS.

DISCLOSURE OF INVENTION

An object of the invention is to provide a novel anti-HIV composition.

Another object of the invention is to provide a novel anti-HIV activity potentiating composition.

A further object of the invention is to provide a novel method for treating syndromes after HIV infection.

Other objects and features of the invention will become apparent from the following description.

To overcome the prior art problems, the inventors of the present invention carried out intensive research on synthetic 2'-deoxynucleosides from diversified viewpoints and found that trifluridine and derivatives thereof have potent anti-HIV activity. The inventors further found that the use of a thymidine phosphorylase inhibitor in combination with trifluridine or its derivatives can reduce the side effects of trifluridine and its derivatives and also retain the in vivo concentration of trifluridine at a level effective for the treatment of HIV infection, thereby enhancing the anti-HIV activity of trifluridine and derivatives thereof. The present invention has been accomplished based on these novel findings.

The present invention provides an anti-HIV composition comprising at least one member selected from the group consisting of trifluridine and derivatives thereof, and a pharmaceutically acceptable carrier.

The present invention further provides an anti-HIV composition comprising (a) at least one member selected from the group consisting of trifluridine and derivatives thereof, (b) a thymidine phosphorylase inhibitor, and a pharmaceutically acceptable carrier.

The present invention further provides a composition for potentiating the anti-HIV activity of trifluridine and derivatives thereof, comprising a thymidine phosphorylase inhibitor and a pharmaceutically acceptable carrier.

The present invention further provides the use of at least one member selected from the group consisting of trifluridine and derivatives thereof for preparing the above anti-HIV compositions.

The present invention further provides a method for treating HIV infection, comprising administering an effective amount of one of the above anti-HIV compositions to HIV-infected mammals, including humans.

The present invention further provides the use of a thymidine phosphorylase inhibitor for preparing a composition for potentiating the anti-HIV activity of trifluridine or derivatives thereof.

The anti-HIV composition of the invention is useful for treating syndromes after HIV infection. The anti-HIV activity potentiating composition of the invention greatly enhances the anti-HIV activity of trifluridine and derivatives thereof.

The trifluridine or derivative thereof used as an active ingredient of the anti-HIV composition of the invention may be trifluridine or any compound that is converted into trifluridine in vivo.

Preferable examples of trifluridine and derivatives thereof are compounds represented by the formula

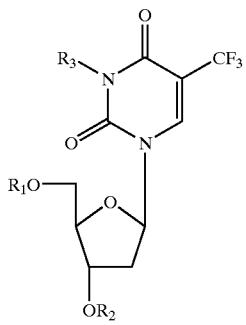

(1)

wherein $R_1$ and $R_2$ may be the same or different and are hydrogen, acyl, lower alkyl, alkoxy-lower alkyl, tetrahydrofuryl, tetrahydropyranyl, triphenylmethyl, benzyloxy-lower alkyl, tetrahydrofuryloxy-lower alkyl, lower alkylcarbamoyl, lower alkoxycarbonyl, tri-substituted silyl, di-substituted phosphoric acid group, benzyl or benzoyl; the three substituents of the tri-substituted silyl group and the two substituents of the di-substituted phosphoric acid group are selected from the group consisting of lower alkyl, phenyl and benzyl and may be the same or different from each other; $R_3$ represents hydrogen, tetrahydrofuryl or benzoyl; when $R_1$ or $R_2$ is benzyl, the benzyl may have one or more substituents selected from the group consisting of lower alkyl, lower alkoxy and halogen; when $R_1$, $R_2$ or $R_3$ is benzoyl, the benzoyl may have one or more substituents selected from the group consisting of lower alkyl, lower alkoxy and halogen.

Among the compounds of formula (1), trifluridine is a compound in which $R_1$, $R_2$ and $R_3$ are all hydrogen. The compounds of formula (1) other than this one are converted into trifluridine in vivo and thus function as prodrugs of trifluridine.

Useful trifluridine derivatives also include the antitumor compounds described in Japanese Unexamined Patent Publications Nos. 152898/1983, 36696/1984, 216899/1984, 56996/1985 and 261396/1989 and WO90/00557.

In the compound of formula (1), when $R_1$ or $R_2$ is acyl, the acyl can be a straight or branched acyl group preferably having 2 to 20 carbon atoms, particularly 2 to 10 carbon atoms. Specific examples include acetyl, n-butyryl, i-butyryl, t-butyl, hexanoyl, isohexanoyl and decanoyl.

When $R_1$ or $R_2$ is lower alkyl, the lower alkyl can be a $C_{1-6}$ straight or branched alkyl group. Specific examples include methyl, ethyl, n-propyl, i-propyl, n-butyl, i-butyl, sec-butyl, t-butyl, hexyl and isohexyl.

When $R_1$ or $R_2$ is alkoxy-lower alkyl, the alkoxy-lower alkyl can be a $C_{1-6}$, particularly $C_{1-3}$, straight or branched alkyl group substituted with a $C_{1-6}$ straight or branched alkoxy group. Examples of the substituent alkoxy group include methoxy, ethoxy, n-butoxy, i-butoxy and t-butoxy. Examples of the alkoxy-lower alkyl group include methoxymethyl, ethoxymethyl and 1-ethoxyethyl.

When $R_1$ or $R_2$ is benzyloxy-lower alkyl, the benzyloxy-lower alkyl can be a $C_{1-6}$, particularly $C_{1-3}$, straight or branched alkyl group substituted with a benzyloxy group. Specific examples include benzyloxymethyl and 1-benzyloxyethyl.

When $R_1$ or $R_2$ is tetrahydrofuryloxy-lower alkyl, the tetrahydrofuryloxy-lower alkyl can be a $C_{1-6}$, particularly $C_{1-3}$, straight or branched alkyl groups substituted with a tetrahydrofuryloxy group. Specific examples include tetrahydrofuryloxymethyl.

When $R_1$, $R_2$ or $R_3$ is tetrahydrofuryl, examples thereof include 2-tetrahydrofuryl.

When $R_1$ or $R_2$ is tetrahydropyranyl, examples thereof include 2-tetrahydropyranyl.

When $R_1$ or $R_2$ is lower alkylcarbamoyl, the lower alkylcarbamoyl can be a carbamoyl group substituted with one or two $C_{1-6}$ straight or branched alkyl groups. Specific examples include methylcarbamoyl, ethylcarbamoyl, n-butylcarbamoyl, i-butylcarbamoyl, t-butylcarbamoyl, hexylcarbamoyl and isohexylcarbamoyl.

When $R_1$ or $R_2$ is lower alkoxycarbonyl, the lower alkoxycarbonyl can be a carbonyl group combined with a $C_{1-6}$ straight or branched alkoxyl group. Specific examples include methoxycarbonyl, ethoxycarbonyl, n-butoxycarbonyl, i-butoxycarbonyl, t-butoxycarbonyl, hexyloxycarbonyl and isohexyloxycarbonyl.

When $R_1$ or $R_2$ is tri-substituted silyl, the tri-substituted silyl can be a silyl group having three identical or different substituents selected from the group consisting of $C_{1-6}$ lower alkyl, phenyl and benzyl. Specific examples include triethylsilyl, t-butyldimethylsilyl, triphenylsilyl, tribenzylsilyl, benzyldimethylsilyl and diphenylmethylsilyl.

When $R_1$ or $R_2$ is di-substituted phosphoric acid group, the di-substituted phosphoric acid group is a phosphoric acid group having two identical or different substituents selected from the group consisting of $C_{1-6}$ lower alkyl, phenyl and benzyl. Specific examples include diethyl phosphoric acid group, diphenyl phosphoric acid group and dibenzyl phosphoric acid group.

When $R_1$, $R_2$ or $R_3$ is benzoyl or when $R_1$ or $R_2$ is benzyl, the benzoyl and the benzyl may have 1 to 5 substituents, preferably 1 to 2 substituents, selected from the group consisting of lower alkyl, lower alkoxy and halogen. The substituent lower alkyl group can be a $C_{1-6}$, preferably $C_{1-4}$, straight or branched alkyl group. Specific examples include methyl, ethyl, n-propyl, i-propyl, n-butyl, i-butyl, sec-butyl and t-butyl. The substituent lower alkoxy group includes a $C_{1-6}$ straight or branched alkoxy group. Specific examples include methoxy, ethoxy, n-propoxy, i-propoxy, n-butoxy, i-butoxy, sec-butoxy and t-butoxy. The substituent halogen atom includes fluorine, chlorine, bromine and iodine.

The substituted benzoyl group includes 4-fluorobenzoyl, 4-chlorobenzoyl, 3-fluorobenzoyl, 2-methoxybenzoyl, 4-methylbenzoyl and 4-butylbenzoyl.

Of the compounds of formula (1), preferred are compounds in which $R_1$ and $R_2$ may be the same or different and are hydrogen, acetyl or 2-tetrahydrofuryl and $R_3$ is 2-tetrahydrofuryl, benzoyl, 4-fluorobenzoyl, 4-chlorobenzoyl, 3-fluorobenzoyl, 2-methoxybenzoyl, 4-methylbenzoyl or 4-butylbenzoyl; compounds in which $R_1$ and $R_2$ may be the same or different and are hydrogen, hexyl, 4-methylbenzoyl, 2-tetrahydrofuryl or t-butyldimethylsilyl and $R_3$ is hydrogen; and the compound in which $R_1$, $R_2$ and $R_3$ are all hydrogen.

A thymidine phosphorylase inhibitor may be included, together with trifluridine or derivatives thereof, in the anti-HIV composition of the invention or can be used singly as a composition for potentiating the anti-HIV activity of trifluridine and derivatives thereof. Examples of the inhibitor include any compounds that can reduce the side effects of trifluridine or its derivatives and also retain the in vivo concentration at which trifluridine or its derivatives can produce anti-HIV effects.

Preferably used as the thymidine phosphorylase inhibitor of the invention are, for example, 6-amino-5-bromouracil, 6-aminothymine, 6-amino-5-chlorouracil, 3-cyano-2,6-dihydroxypyridine, acyclothymidine, or pharmaceutically acceptable salts of these compounds.

Examples of compounds preferably used as the thymidine phosphorylase inhibitor of the invention further include pyrimidinedione derivatives represented by the formula

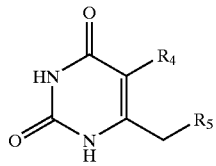

(2)

wherein $R_4$ is chlorine, bromine, iodine, cyano or lower alkyl. $R_5$ is a 4- to 8-membered heterocyclic group containing 1 to 3 nitrogen atoms and optionally having one or more substituents selected from the group consisting of lower alkyl, imino, hydroxyl, hydroxymethyl, methanesulfonyloxy, amino and nitro; an amidinothio group in which one or more of the hydrogen atoms on the nitrogen atom may be substituted by lower alkyl groups; a guanidino group in which one or more hydrogen atoms on the nitrogen atom may be substituted by lower alkyl or cyano groups; a lower alkylamidino group; an amino group in which one or more of the hydrogen atoms on the nitrogen atom may be substituted by lower alkyl groups; —$CH_2N(Ra)$ (Rb) (in which Ra and Rb may be the same or different and are hydrogen or lower alkyl, or Ra and Rb, together with the nitrogen atom to which they are attached, may form a pyrrolidine ring); —NH—$(CH_2)_m$—Z (in which Z is a cyano group or an amino group in which one or more of the hydrogen atoms on the nitrogen atom may be substituted by lower alkyl groups, and m is an integer of 0 to 3); —NRc$(CH_2)_n$—OH (in which Rc is hydrogen or lower alkyl and n is an integer of 1 to 4); a group —X—Y (in which X is S or NH and Y is optionally lower alkyl-substituted 2-imidazolin-2-yl, 2-imidazolyl, 1-methylimidazol-2-yl, 1,2,4-triazol-3-yl, 2-pyrimidyl or 2-benzimidazolyl); or ureido or thioureido in which one or more of the hydrogen atoms on the nitrogen atom may be substituted by lower alkyl groups; and pharmaceutically acceptable salts thereof.

The thymidine phosphorylase inhibitor is a known compound described in Biochemical Pharmacology, vol. 29, 1059(1980), Japanese Unexamined Patent Publications Nos. 250324/1988 and 213761/1993, WO96/30346, etc.

In the pyrimidinedione derivative of formula (2), when $R_4$ is lower alkyl, the lower alkyl can be a $C_{1-4}$ straight or branched alkyl group. Specific examples include methyl, ethyl, n-propyl, i-propyl, n-butyl, i-butyl, sec-butyl and t-butyl. Especially preferred is methyl.

When $R_5$ is a 4- to 8-membered heterocyclic group having 1 to 3 nitrogen atoms, specific examples include 1-azetidinyl, 1-pyrrolidinyl, 2-pyrrolin-1-yl, 3-pyrrolin-1-yl, 1-pyrrolyl, 1-pyrazolidinyl, 2-pyrazolin-1- yl, 3-pyrazolin-1-yl, 4-pyrazolin-1-yl, 1-pyrazolyl, 1-imidazolidinyl, 2-imidazolin-1-yl, 3-imidazolin-1-yl, 4-imidazolin-1-yl, 1-imidazolyl, 1,2,3-triazol-1-yl, 1,2,4-triazol-1-yl, piperidino, 1-piperazyl, morpholino, 1-perhydroazepinyl and 1-perhydroazocinyl.

The heterocyclic group may have one or two substituents on the ring. Examples of substituents include lower alkyl, imino, hydroxyl, hydroxymethyl, methanesulfonyloxy, amino and nitro. The substituent lower alkyl group can be a $C_{1-4}$ straight or branched alkyl group and specific examples include methyl, ethyl, n-propyl, i-propyl, n-butyl, i-butyl, sec-butyl and t-butyl. Especially preferred is methyl.

Specific examples of heterocyclic groups which may have one or two substituents include 1-azetidinyl, 1-pyrrolidinyl, 2,5-dimethylpyrrolidin-1-yl, 2-iminopyrrolidin-1-yl, 3-hydroxypyrrolidin-1-yl, 2-hydroxymethylpyrrolidin-1-yl, 3-methanesulfonyloxypyrrolidin-1-yl, 3-aminopyrrolidin-1-yl, 2-pyrrolin-1-yl, 3-pyrrolin-1-yl, 2-imino-3-pyrrolin-1-yl, 1-pyrrolyl, 1-pyrazolidinyl, 2-methylpyrazolidin-1-yl, 4-iminopyrazolidin-1-yl, 2-pyrazolin-1-yl, 3-pyrazolin-1-yl, 2-methyl-3-pyrazolin-1-yl, 5-imino-3-pyrazolin-1-yl, 4-pyrazolin-1-yl, 2-methyl-4-pyrazolin-1-yl, 3-imino-4-pyrazolin-1-yl, 1-pyrazolyl, 1-imidazolidinyl, 3-methylimidazolidin-1-yl, 2-iminoimidazolidin-1-yl, 2-imino-3-methylimidazolidin-1-yl, 2-imino-3-ethylimidazolidin-1-yl, 2-imino-3-isopropylimidazolidin-1-yl, 2-imidazolin-1-yl, 3-imidazolin-1-yl, 4-imidazolin-1-yl, 3-methyl-4-imidazolin-1-yl, 2-imino-4-imidazolin-1-yl, 2-imino-3-methyl-4-imidazolin-1-yl, 2-imino-3-ethyl-4-imidazolin-1-yl, 2-imino-3-isopropyl-4-imidazolin-1-yl, 1-imidazolyl, 2-methylimidazol-1-yl, 2-nitroimidazol-1-yl, 4-nitroimidazol-1-yl, 1,2,3-triazol-1-yl, 1,2,4-triazol-1-yl, 3-nitro-1,2,4-triazol-1-yl, piperidino, 1-piperazyl, 4-methylpiperazin-1-yl, morpholino, 1-perhydroazepinyl and 1-perhydroazocinyl. Preferable are 1-azetidinyl, 1-pyrrolidinyl, 2-iminopyrrolydin-1-yl, 2-iminoimidazolidin-1-yl, 2-imino-3-methylimidazolidin-1-yl, 2-imino-3-ethylimidazolidin-1-yl, 2-imino-3-isopropylimidazolidin-1-yl, 2-imidazolin-1-yl, 2-imino-3-methyl-4-imidazolin-1-yl, 2-imino-3-ethyl-4-imidazolin-1-yl and 1-imidazolyl.

When $R_5$ is an amidinothio group in which one or more of the hydrogen atoms on the nitrogen atom may be substituted by a like number of lower alkyl groups, one to three of the three hydrogen atoms on the nitrogen atom of the amidino group may be substituted by the above-exemplified lower alkyl groups. Especially preferred are amidinothio, $N^1$-methylamidinothio and $N^1,N^2$-dimethyl amidinothio.

When $R_5$ is a guanidino group in which one or more of the hydrogen atoms on the nitrogen atom may be substituted by a like number of lower alkyl or cyano groups, one to four of the four hydrogen atoms of the guanidino group may be substituted by a like number of the above-exemplified lower alkyl groups or cyano. Especially preferred are 1-guanidino, 1-methylguanidino, 3-methylguanidino, 2,3-dimethylguanidino and 2-cyano-3-methylguanidino.

When $R_5$ is lower alkylamidino, the lower alkylamidino is an amidino group to which a lower alkyl group as exemplified above is attached. Especially preferred is acetoamidino.

When $R_5$ is an amino group in which one or more of the hydrogen atoms on the nitrogen atom may be substituted by a like number of lower alkyl groups, one or two of the two hydrogen atoms of the amino group may be substituted by a like number of lower alkyl groups exemplified above. Especially preferred are amino, N-methylamino, N,N-dimethylamino, N-ethylamino, N,N-diethylamino, N-propylamino and N-isopropylamino.

When $R_5$ is —$CH_2N(Ra)$ (Rb), preferable examples are N-methylaminomethyl, N,N-dimethylaminomethyl and 1-pyrrolidinylmetyl.

When $R_5$ is —NH—$(CH_2)_m$—Z, preferable examples are N,N-dimethylhydrazino, N-(2-aminoethyl)amino, N-(2-(N, N-dimethyl)aminoethyl)amino, N-(3-aminopropyl) amino and N-(2-cyanoethyl)amino.

When $R_5$ is —NRc$(CH_2)_n$—OH, preferable examples are N-(2-hydroxyethyl)-N-methylamino, N-(3-hydroxypropyl) amino and N-(4-hydroxybutyl)amino.

When $R_5$ is a group —X—Y, preferable examples are 2-imidazolin-2-thio, 2-imidazolin-2-amino, imidazol-2-thio, 1-methylimidazol-2-thio, 1,2,4-triazol-3-thio, pyrimidine-2-thio and benzimidazol-2-thio.

When $R_5$ is ureido or thioureido in which one or more hydrogen atoms on the nitrogen atom may be substituted by a like number of lower alkyl groups, preferable examples include 3-methylthioureido.

Preferably, $R_5$ in formula (2) is a 4- to 8-membered heterocyclic group containing 1 to 3 nitrogen atoms and optionally having one or more substituents selected from the group consisting of lower alkyl, imino, hydroxyl, hydroxymethyl, methanesulfonyloxy, amino and nitro; an amidinothio group in which one or more of the hydrogens on the nitrogen atom may be substituted by a like number of lower alkyl groups; a guanidino group in which one or more of the hydrogen atoms on the nitrogen may be substituted by a like number of lower alkyl or cyano groups; or a lower alkylamidino group.

More specifically, $R_5$ is preferably 1-azetidinyl, 1-pyrrolidinyl, 2-iminopyrrolidin-1-yl, 2-iminoimidazolidin-1-yl, 2-imino-3- methylimidazolydin-1-yl, 2-imino-3-ethylimidazolidin-1-yl, 2-imino-3-isopropylimidazolidin-1-yl, 2-imidazolin-1-yl, 2-imino-3-methyl-4-imidazolin-1-yl, 2-imino-3-ethyl-4-imidazolin-1-yl, 1-imidazolyl, amidinothio, $N^1$-methylamidinothio, $N^1,N^2$-dimethylamidinothio, 1-guanidino, 1-methylguanidino, 3-methylguanidino, 2,3-dimethylguanidino or acetoamidino.

The pyrimidinedione derivative of formula (2) is preferably a compound in which $R_4$ is chlorine, bromine or cyano and $R_5$ is 1-pyrrolidinyl, 1-azetidinyl, 2-iminopyrrolidin-1-yl, 2-iminoimidazolidin-1-yl, 1-imidazolyl, amidinothio or 1-guanidino.

The pharmaceutically acceptable salt of the pyrimidinedione derivative is not particularly limited. Preferred are acid addition salts and/or base salts formed by reacting the pyrimidinedione derivative with a pharmaceutically acceptable acid or basic compound. Examples of such acid addition salts include salts of inorganic acids such as hydrochloric acid, sulfuric acid, phosphoric acid and hydrobromic acid; salts of organic acids such as oxalic acid, maleic acid, fumaric acid, malic acid, tartaric acid, citric acid, benzoic acid, acetic acid, p-toluenesulfonic acid and methanesulfonic acid. Preferred are salts of hydrochloric acid or p-toluenesulfonic acid. Examples of base salts include salts of alkali metals or alkaline earth metals such as sodium, potassium, magnesium and calcium; salts of amines such as ammonia, methylamine, dimethylamine, piperidine, cyclohexylamine and triethylamine.

Of the compounds usable as the thymidine phosphorylase inhibitor, preferred are the compounds of formula (2) including 5-chloro-6-(2-iminopyrrolidin-1-yl)methyl-2,4(1H,3H)-pyrimidinedione, 5-bromo-6-(1-pyrrolidinyl)methyl-2,4(1H,3H)-pyrimidinedione, 5-cyano-6-(2-iminopyrrolidin-1-yl)methyl-2,4(1H,3H)-pyrimidinedione, 5-chloro-6-(2-iminoimidazolidin-1-yl)methyl-2,4(1H,3H)-pyrimidinedione, or pharmaceutically acceptable salts of these compounds.

Of the compounds usable as the thymidine phosphorylase inhibitor, especially preferred are 5-chloro-6-(2-iminopyrrolidin-1-yl)methyl-2,4(1H,3H)-pyrimidinedione hydrochloride and 5-chloro-6-(2-iminopyrrolidin-1-yl)methyl-2,4(1H,3H)-pyrimidinedione tosylate.

In the present invention, at least one member selected from the group consisting of trifluridine and derivatives thereof, and the thymidine phosphorylase inhibitor can be separately formulated in the desired unit dosage forms and administered independently or simultaneously. In the case of independent administration, the thymidine phosphorylase inhibitor can be administered at any time before or after the administration of trifluridine or a derivative thereof. The thymidine phosphorylase inhibitor is preferably administered within the period from about 4 hours before, to about 4 hours after the administration of trifluridine or a derivative thereof, more preferably from about 1 hour before, to about 1 hour after the administration.

Alternatively, an anti-HIV composition containing at least one member selected from the group consisting of trifluridine and derivatives thereof, and the thymidine phosphorylase inhibitor can be formulated in the desired unit dosage form and administered. In this case, the blending ratio of the at least one member selected from the group consisting of trifluridine and derivatives thereof to the thymidine phosphorylase inhibitor is not particularly limited. However, the latter is usually blended in a proportion of about 0.05 to about 20 moles, preferably 0.1 to 5 moles, per mole of the former.

When 5-chloro-6-(2-iminopyrrolidin-1-yl)methyl-2,4(1H,3H)-pyrimidinedione or a pharmaceutically acceptable salt thereof is used as the thymidinephosphorylase inhibitor, the molar ratio of the inhibitor to the at least one member selected from the group consisting of trifluridine and derivatives thereof is usually about 0.05:1 to about 20:1, preferably about 0.1:1 to about 5:1.

When trifluridine derivatives are used in combination, the amount of such inhibitors is calculated based on the assumption that the trifluridine derivatives are 100% converted into trifluridine in vivo and expressed relative to 1 mole of trifluridine.

When the anti-HIV composition containing as an active ingredient at least one member selected from the group consisting of trifluridine and derivatives thereof, the anti-HIV composition containing as active ingredients at least one member selected from the group consisting of trifluridine and derivatives thereof and the thymidine phosphorylase inhibitor, or the anti-HIV activity potentiating composition containing the inhibitor as an active ingredient is to be used as a therapeutic drug for HIV infections in mammals, including humans, the composition can be formulated into a pharmaceutically suitable dosage form according to the therapeutic purpose.

More specifically, the composition can be formulated into oral dosage forms such as tablets, coated tablets, pills, powders, granules, capsules, liquids, suspensions and emulsions; and parenteral dosage forms such as injections and suppositories. Such dosage forms of the composition can be manufactured using pharmaceutically acceptable carriers by known procedures conventionally used in the art.

When manufacturing tablets, useful carriers include excipients such as lactose, saccharose, sodium chloride, glucose, urea, starch, calcium carbonate, kaolin, crystalline cellulose and silicic acid; binders such as water, ethanol, propanol, corn starch, simple syrup, liquid glucose, liquid starch, gelatin solution, carboxymethylcellulose, shellac, methyl cellulose, hydroxypropylcellulose, hydroxypropyl methylcellulose, potassium phosphate and polyvinylpyrrolidone; disintegrators such as dried starch, sodium alginate, agar powder, laminaran powder, sodium hydrogencarbonate, calcium carbonate, polyoxyethylene sorbitan fatty acid ester, sodium lauryl sulfate, stearic acid monoglyceride, starch and lactose; disintegration inhibitors such as sucrose, stearic acid, cacao butter and hydrogenated oil; absorption promoters such as quaternary ammonium base and sodium lauryl sulfate; humectants such as glycerin and starch; adsorbents such as starch, lactose, kaolin, bentonite and colloidal silicic acid; and lubricants such as purified talc, stearic acid salt, boric acid powder and polyethylene glycol. The tablets may further be made into coated tablets such as sugar-coated tablets, gelatin-coated tablets, enteric tablets, film-coated tablets, double-layered tablets or multiple-layered tablets.

When preparing pills by molding, useful carriers include excipients such as glucose, lactose, starch, cacao butter, hydrogenated vegetable oil, kaolin and talc; binders such as gum arabic powder, tragacanth powder, gelatin and ethanol; and disintegrators such as laminaran and agar.

Capsules are usually manufactured in a conventional manner by blending the active ingredient of the invention with one or more carriers as exemplified above and encapsulating the mixture into hard gelatin capsule shells, soft capsule shells, etc.

When preparing oral liquid preparations, useful additives include corrigents, buffers, stabilizers, aroma corrigent, etc. and oral solutions, syrups and elixirs can be manufactured by conventional methods. Useful as corrigents are white sugar, bitter orange peel, citric acid, tartaric acid, etc. Useful buffers include sodium citrate and useful stabilizers include gum tragacanth, gum arabic and gelatin.

When manufacturing suppositories, useful carriers include polyethylene glycol, cacao butter, a higher alcohol or esters thereof, gelatin and semisynthetic glyceride.

When the pharmaceutical preparation is to be provided in an injectable form such as a solution, an emulsion or a suspension, the preparation is preferably sterilized and rendered isotonic to the blood. Diluents usable for such a preparation are, for example, water, aqueous lactic acid solution, ethanol, propylene glycol, macrogols, ethoxylated isostearyl alcohol, polyoxylated isostearyl alcohol, and polyoxyethylene sorbitan fatty acid ester. In this case, sodium chloride, glucose or glycerin may be added to the pharmaceutical composition in an amount sufficient to provide an isotonic solution. Conventional solubilizers, buffers, anesthetics and the like may also be added to the pharmaceutical composition.

Further, coloring agents, preservatives, aromatics, flavors, sweeteners or other medicines may be incorporated, if desired, into the pharmaceutical composition.

The amounts of the at least one member selected from the group consisting of trifluridine and derivatives thereof, and the thymidine phosphorylase inhibitor in the pharmaceutical composition of the invention are not very critical and can be appropriately selected from a broad range. In general, the amount ofeach is preferably about 1–70 wt. % in the pharmaceutical composition.

The anti-HIV composition or the anti-HIV activity potentiating composition of the invention is administered to mammals, including humans. There is no limitation on the mode of administration. A suitable mode can be selected according to the dosage form, the patient's age, sex and other factors, and the severity of disease. For example, tablets, pills, powders, granules, capsules, solutions (liquids), suspensions and emulsions are orally administered. The preparations in injection form are intravenously administered singly or in admixture with a conventional infusion liquid such as liquid glucose or an amino acid liquid. Further, if necessary, the injections are singly administered intra-arterially, intramuscularly, intradermally, subcutaneously or intraperitoneally. The suppositories are administered intrarectally.

The dosage of the active ingredients of the anti-HIV composition and the anti-HIV activity potentiating composition of the invention can be suitably selected according to the mode of administration, the patient's age, sex and other factors, and the severity of disease. The dosage of the trifluridine derivative is usually about 0.01 to about 50 mg per kg body weight a day for a human adult, preferably about 0.1 to about 20 mg/kg/day. The dosage of the thymidine phosphorylase inhibitor is usually about 0.01 to about 100 mg per kg body weight a day for a human adult, preferably about 0.05 to about 50 mg/kg/day. These pharmaceutical preparations of the invention may be administered once a day or in 2–4 divided doses a day.

BEST MODE FOR CARRYING OUT THE INVENTION

Reference Examples, Formulation Examples and Test Examples are given below to illustrate the invention in more detail, but it is to be understood that the invention is not limited thereto.

REFERENCE EXAMPLE 1

Synthesis of 5-Chloro-6-(2-iminopyrrolidin-1-yl) methyl-2,4(1H,3H)-pyrimidinedione Hydrochloride (Compound 1)

Sulfulyl chloride (120 ml) was added dropwise to a suspension of 163 g of 6-chloromethyluracil in 500 ml of acetic acid at room temperature for 20 minutes and stirred at the same temperature for 3 hours. The reaction mixture was poured into ice water (500 ml) and the resulting crystals were collected by filtration to give 182.3 g of 5-chloro-6-chloromethyluracil (yield 92%). The physical properties of this compound are as follows:

mp: $\geq 225°$ C. (decomp.); NMR spectrum (DMSO-$d_6$)δ: 4.46(2H, s), 11.57(1H, s), 11.71(1H, s).

A solution of 5.0 g of 5-chloro-6-chloromethyluracil, 6.14 g of 2-imino pyrrolidine and 5.24 g of sodium ethoxide in 50 ml of N,N-dimethylformamide was stirred at room temperature for 14 hours. The resulting crystals were collected by filtration and suspended in 30 ml of water. The suspension was neutralized with acetic acid and washed. The insoluble substances were collected by filtration and dissolved in 60 ml of 1N hydrochloric acid. After addition of activated carbon, the resulting mixture was filtered. The filtrate was concentrated under reduced pressure and the residue was washed with ethanol and collected by filtration, giving 2.68 g of the desired compound (yield 38%). The physical properties of this compound are as follows:

mp: $\geq 255°$ C. (decomp.); NMR spectrum (DMSO-$d_6$)δ: 2.04(2H, quintet, J=7.6 Hz), 2.87(2H, t, J=7.6 Hz), 3.59(2H, t, J=7.6 Hz), 4.69(2H, s), 9.40(1H, s), 11.46(1H, s), 11.73 (1H, s).

REFERENCE EXAMPLE 2

Synthesis of 5-Chloro-6-(2-iminopyrrolidin-1-yl) methyl-2,4(1H,3H)-pyrimidinedione Tosylate (Compound 2)

The procedure of Reference Example 1 was repeated except that p-toluenesulfonic acid was used in place of iN hydrochloric acid. The title compound was obtained in a yield of 26%. The physical properties of this compound are as follows:

mp: $\geq 210°$ C. (decomp.); NMR spectrum (DMSO-$d_6$)δ: 2.05(2H, quintet, J=7.7 Hz), 2.29(3H, s), 2.87(2H, t, J=7.7 Hz), 3.60(2H, t, J=7.7 Hz), 4.56(2H, s), 7.11(2H, d, J=7.3 Hz), 7.47(2H, d, J=7.3 Hz), 9.51(1H, br-s), 11.0–11.8(2H, very br).

FORMULATION EXAMPLE 1

Single Active Ingredient Formulation for Oral Administration

| | |
|---|---|
| Trifluridine | 30.0 mg |
| Lactose | 8.0 mg |
| Crystalline cellulose | 4.0 mg |
| Magnesium stearate | 1.0 mg |
| Talc | 1.0 mg |
| Corn starch | 3.5 mg |
| Hydroxypropyl methylcellulose | 2.5 mg |
| Per tablet | 50.0 mg |

According to the above formulation, tablets were manufactured in a conventional manner.

FORMULATION EXAMPLE 2

Single Active Ingredient Formulation for Oral Administration

| | |
|---|---|
| Compound 1 obtained in Reference Example 1 | 14.0 mg |
| Lactose | 4.0 mg |
| Crystalline cellulose | 2.0 mg |
| Magnesium stearate | 1.0 mg |
| Talc | 1.0 mg |
| Corn starch | 3.5 mg |
| Hydroxypropyl methylcellulose | 2.5 mg |
| Per tablet | 28.0 mg |

According to the above formulation, tablets were manufactured in a conventional manner.

FORMULATION EXAMPLE 3

Multiple Active Ingredient Formulation for Oral Administration

| | |
|---|---|
| Trifluridine | 50.0 mg |
| Compound 1 obtained in Reference Example 1 | 24.0 mg |
| Lactose | 83.0 mg |
| Corn starch | 100.0 mg |
| Hydroxypropyl methylcellulose | 3.0 mg |
| Per pack | 240.0 mg |

According to the above formulation, granules were manufactured in a conventional manner.

FORMULATION EXAMPLE 4

Multiple Active Ingredient Formulation for Oral Administration

| | |
|---|---|
| Trifluridine | 10.0 mg |
| Compound 1 obtained in Reference Example 1 | 180.0 mg |
| Lactose | 83.0 mg |
| Corn starch | 100.0 mg |
| Hydroxypropyl methylcellulose | 3.0 mg |
| Per pack | 376.0 mg |

According to the above formulation, granules were manufactured in a conventional manner.

FORMULATION EXAMPLE 5

Multiple Active Ingredient Formulation for Oral Administration

| | |
|---|---|
| Trifluridine | 30.0 mg |
| Compound 2 obtained in Reference Example 2 | 140.0 mg |
| Lactose | 24.0 mg |
| Crystalline cellulose | 13.0 mg |
| Magnesium stearate | 1.0 mg |
| Per capsule | 208.0 mg |

According to the above formulation, capsules were manufactured in a conventional manner.

FORMULATION EXAMPLE 6

Multiple Active Ingredient Formulation for Oral Administration

| | |
|---|---|
| Trifluridine | 20.0 mg |
| Compound 1 obtained in Reference Example 1 | 1.0 mg |
| Lactose | 4.0 mg |
| Crystalline cellulose | 2.0 mg |
| Magnesium stearate | 1.0 mg |
| Talc | 1.0 mg |
| Corn starch | 3.0 mg |
| Hydroxypropyl methylcellulose | 2.0 mg |
| Per tablet | 34.0 mg |

According to the above formulation, tablets were manufactured in a conventional manner.

FORMULATION EXAMPLE 7

Multiple Active Ingredient Formulation for Injection

| | |
|---|---|
| Trifluridine | 5.0 mg |
| Compound 1 obtained in Reference Example 1 | 1.0 mg |
| Distilled water for injection | q.s. |
| Per ampoule | 5.0 ml |

According to the above formulation per ampoule, an injection was manufactured in a conventional manner.

FORMULATION EXAMPLE 8

Multiple Active Ingredient Formulation for Suppository

| | |
|---|---|
| Trifluridine | 50.0 mg |
| Compound 1 obtained in Reference Example 1 | 24.0 mg |
| Witepsol W-35 (trade name, product of Dynamit Nobel AG) | 1426.0 mg |
| Per suppository | 1500.0 mg |

According to the above formulation, a suppository was manufactured in a conventional manner.

PHARMACOLOGICAL TEST

TEST EXAMPLE 1

Antiviral activity against HIV GUN-1 strain (Jpn. J. Cancer Res., vol. 78, 11–15(1987)) and HIV IIIB strain (Science, vol. 224, 497–500(1984)) in MT-2 cells and MT-4 cells (Nature, vol. 294, 770–771 (1981))

MT-2 cells and MT-4 cells were transferred to RPMI 1640 medium (supplemented with 10% fetal calf serum (FCS)) at $2 \times 10^5$ cells/ml. To each 500 µl of the medium, a different concentration of trifluridine solution (hereinafter referred to as FTD) or a trifluridine-free solution was added. The cells were cultured at 37° C. One hour later, the cells were infected with HIV at multiplicity of infection of 0.05 (MOI= 0.05) and cultured at 37° C. for 2 days. Smears of MT-2 cells and MT-4 cells were prepared and assayed for HIV-positive cells by fluorescent antibody assay (Science, vol. 229, 563(1985)). 3'-Azide-3'-deoxythymidine (hereinafter abbreviated as AZT) was used as a positive control.

The relative infection rate (%), expressed as a percentage, was calculated from the number of HIV-infected cells in the drug-treated group relative to the number of infected cells in the drug-free solution-treated group as a control group by the following equation:

Relative infection rate (%)=($N_1/N_2$)×100 in which $N_1$ is the number of HIV-positive cells in the test drug-treated group, and $N_2$ is the number of HIV-positive cells in the control group.

As an indication of the anti-HIV GUN-1 activity, Table 1 shows the infection rates (%) of the test groups treated with the test drug solutions of different concentrations, relative to the infection rate (100%) of the control group.

TABLE 1

| | | Drug concentration (μg/ml) | | | | | | | |
|---|---|---|---|---|---|---|---|---|---|
| Test drug | Cells | 1000 | 100 | 10 | 1 | 0.1 | 0.01 | 0.001 | 0 (Control group) |
| FTD | MT-2 | 0 | 0 | 0 | 50 | 100 | 100 | 100 | 100 |
| | MT-4 | 0 | 0 | 0.4 | 10 | 100 | 100 | 100 | 100 |
| AZT | MT-2 | 0 | 0 | 0 | 0 | 10 | 30 | 100 | 100 |
| | MT-4 | 0 | 0 | 0 | 0 | 4 | 40 | 100 | 100 |

As an indication of the anti-HIV IIIB activity, Table 2 shows the infection rates (%) of the test groups treated with the test drug solutions of different concentrations, relative to the infection rate (100%) of the control group.

TABLE 2

| | | Drug concentration (μg/ml) | | | | | | | |
|---|---|---|---|---|---|---|---|---|---|
| Test drug | Cells | 1000 | 100 | 10 | 1 | 0.1 | 0.01 | 0.001 | 0 (Control group) |
| FTD | MT-2 | 0 | 0 | 4 | 20 | 100 | 100 | 100 | 100 |
| | MT-4 | 0 | 0 | 2.5 | 10 | 100 | 100 | 100 | 100 |
| AZT | MT-2 | 0 | 0 | 0 | 0 | 10 | 20 | 100 | 100 |
| | MT-4 | 0 | 0 | 0 | 0 | 5 | 25 | 100 | 100 |

TEST EXAMPLE 2

Cytotoxicity Against MT-2 Cells and MT-4 Cells

MT-2 cells and MT-4 cells were transferred to RPMI 1640 medium (supplemented with 10% FCS) at 2×10⁵ cells/ml. To each 500 μl of the medium, a different concentration of FTD solution or a FTD-free solution was added. The cells were cultured at 37° C. Two days later, the trypan blue exclusion test was carried out and the number of living cells in each group was counted.

Relative survival rate (%), expressed as a percentage, was calculated from the number of living cells in the test drug-treated group relative to the number of living cells in the drug-free solution-treated group as a control group, by the following equation:

Relative survival rate (%)=($N_3/N_4$)×100 in which $N_3$ is the number of living cells in the test drug-treated group, and $N_4$ is the number of living cells in the control group.

Table 3 shows the survival rates (%) of the test groups treated with the test drug solutions of different concentrations, relative to the survival rate (100%) of the control group.

TABLE 3

| | | Drug concentration (μg/ml) | | | |
|---|---|---|---|---|---|
| Test drug | Cells | 1000 | 100 | 10 | 0 (Control group) |
| FTD | MT-2 | 63 | 100 | 100 | 100 |
| | MT-4 | 52 | 100 | 100 | 100 |
| AZT | MT-2 | 100 | 100 | 100 | 100 |
| | MT-4 | 84 | 100 | 100 | 100 |

TEST EXAMPLE 3

Antiviral Activity Against HIV GUN-1 Strain in C8166 Cells (Salahuddinn et al., Virology, vol. 129, 51–64(1983))

C8166 cells were transferred to RPMI 1640 medium (supplemented with 10% FCS) at 2×10⁵ cells/ml. To each 100 μl of the medium, 10 μl of a different concentration of FTD solution or a FTD-free solution was added. The cells were cultured at 37° C. One hour later, the cells were infected with HIV at multiplicity of infection (MOI) of 0.25 (MOI=0.25) and cultured at 37° C. for 2 days. Then the number of syncytia induced by HIV infection was determined.

Relative infection rate (%), expressed as a percentage, was calculated from the number of HIV-infected cells in the test drug-treated group relative to the number of HIV-infected cells in the drug-free solution-treated group as a control group, by the following equation:

Relative infection rate (%)=($N_5/N_6$)×100 in which $N_5$ is the number of syncytia in the test drug-treated group, and $N_6$ is the number of syncytia in the control group.

Table 4 shows the infection rates (%) of the test groups treated with the test drug solutions of different concentrations, relative to the infection rate (100%) of the control group.

Test drug solutions of certain concentrations greatly inhibited the formation of syncytia. The cell survival rates at such concentrations were determined by the trypan blue exclusion test. The cell survival rate (%) was calculated by the following equation:

Survival rate (%)=($N_7/N_8$)×100 in which $N_7$ is the number of living cells in the test drug-treated group, and $N_8$ is the total number of the cells in the test drug-treated group.

Table 4 also shows the cell survival rates (%) at the different concentrations of the test drug solution.

TABLE 4

| | Drug (FTD) concentration (μg/ml) | | | | | | |
|---|---|---|---|---|---|---|---|
| | 1000 | 100 | 10 | 1 | 0.1 | 0.01 | 0 (control group) |
| Infection rate (%) | 0 | 0 | 0 | 2 | 59 | 90 | 100 |
| Survival rate (%) | 93 | 98 | 98 | 97 | NT | NT | NT |

NT: not tested

TEST EXAMPLE 4

Animal Test for Trifluridine (FTD) Toxicity Reducing Action of the Thymidine Phosphorylase Inhibitor FTD alone or in combination with compound 1 prepared in Reference Example 1 (molar ratio of FTD/compound 1=1/0.5) was orally administered repeatedly to male SD rats (Sprague-Dawley rats) and male beagle dogs for 14 days to evaluate the FTD toxicity reducing action of compound 1. Administered to SD rats was 15, 50, 150 or 450 mg/kg of FTD alone in single use (5 rats per group). In combined use, FTD+compound 1 were administered in the amounts of 15+7 mg/kg, 50+24 mg/kg, 150+71 mg/kg or 450+212 mg/kg (5 rats per group).

Administered to beagle dogs was 2, 6 or 17 mg/kg of FTD alone in single use (3 dogs per group). In combined use, FTD+compound 1 were administered in the amounts of 17+8 mg/kg, 50+24 mg/kg or 150+71 mg/kg (3 dogs per group).

Table 5 shows the maximum tolerated dose causing no death (expressed as FTD dose).

TABLE 5

| | Maximum tolerated dose (mg/kg) | |
|---|---|---|
| | SD rats | Beagle dogs |
| FTD + compound 1 | 450 | 17 |
| FTD | 150 | 6 |

As shown in Table 5, the thymidine phosphorylase inhibitor (compound 1) reduced the toxicity of FTD and approximately tripled the maximum tolerated doses in SD rats and beagle dogs.

The anti-HIV composition of the invention has the following advantages:

trifluridine or derivatives thereof have high anti-HIV activity; and the use of a thymidine phosphorylase inhibitor in combination with trifluridine or its derivatives reduces the side effects of trifluridine and its derivatives and can also retain the in vivo concentration of trifluridine at a level effective for the treatment of HIV infection.

Thus the anti-HIV composition of the invention is highly effective for the treatment of syndromes after HIV infection in mammals such as humans and monkeys.

What is claimed is:

1. An anti-HIV composition comprising:
   (a) at least one member selected from the group consisting of trifluridine and derivatives thereof;
   (b) a thymidine phosphorylase inhibitor; and a pharmaceutically acceptable carrier.

2. The anti-HIV composition according to claim 1 wherein the trifluridine derivatives are compounds that can be converted into trifluridine in vivo.

3. The anti-HIV composition according to claim 1 wherein the trifluridine and derivatives thereof are compounds represented by the formula

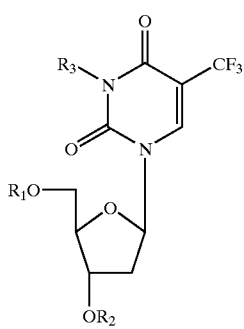

(1)

wherein $R_1$ and $R_2$ may be the same or different and are hydrogen, acyl, lower alkyl, alkoxy-lower alkyl, tetrahydrofuryl, tetrahydropyranyl, triphenylmethyl, benzyloxy-lower alkyl, tetrahydrofuryloxy-lower alkyl, lower alkylcarbamoyl, lower alkoxycarbonyl, tri-substituted silyl, di-substituted phosphoric acid group, benzyl or benzoyl; the three substituents of the tri-substituted silyl group and the two substituents of the di-substituted phosphoric acid group are selected from the group consisting of lower alkyl, phenyl and benzyl and may be the same or different from each other; $R_3$ represents hydrogen, tetrahydrofuryl or benzoyl; when $R_1$ or $R_2$ is benzyl, the benzyl may have one or more substituents selected from the group consisting of lower alkyl, lower alkoxy and halogen; when $R_1$, $R_2$ or $R_3$ is benzoyl, the benzoyl may have one or more substituents selected from the group consisting of lower alkyl, lower alkoxy and halogen.

4. The anti-HIV composition according to claim 1 wherein the thymidine phosphorylase inhibitor is at least one member selected from the group consisting of 6-amino-5-bromouracil, 6-aminothymine, 6-amino-5-chlorouracil, 3-cyano-2,6-dihydroxypyridine, acyclothymidine, and pharmaceutically acceptable salts of these compounds.

5. The anti-HIV composition according to claim 1 wherein the thymidine phosphorylase inhibitor is at least one member selected from the group consisting of pyrimidinedione derivatives represented by the formula

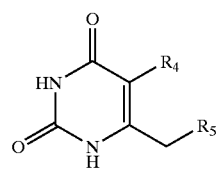

(2)

wherein $R_4$ is chlorine, bromine, iodine, cyano or lower alkyl; and $R_5$ is a 4- to 8-membered heterocyclic group containing 1 to 3 nitrogen atoms and optionally having one or more substituents selected from the group consisting of lower alkyl, imino, hydroxyl, hydroxymethyl, methanesulfonyloxy, amino and nitro; an amidinothio group in which one or more of the hydrogen atoms on the nitrogen atom may be substituted by lower alkyl groups; a guanidino group in which one or more hydrogen atoms on the nitrogen atom may be substituted by lower alkyl or cyano groups; a lower alkylamidino group; an amino group in which one or more of the hydrogen atoms on the nitrogen atom may be substituted by lower alkyl groups; —CH$_2$N(Ra)(Rb) (in which Ra and Rb may be the same or different and are hydrogen or lower alkyl, or Ra and Rb, together with the nitrogen atom to which they are attached, may form a pyrrolidine ring); —NH—(CH$_2$)$_m$—Z (in which Z is a cyano group or an amino group in which one or more of the hydrogen atoms on the nitrogen atom may be substituted by lower alkyl groups, and m is an integer of 0 to 3); —NRc(CH$_2$)$_n$—OH (in which Rc is hydrogen or lower alkyl and n is an integer of 1 to 4); a group —X—Y (in which X is S or NH and Y is optionally lower alkyl-substituted 2-imidazolin-2-yl, 2-imidazolyl, 1-methylimidazol-2-yl, 1,2,4-triazol-3-yl, 2-pyrimidyl or 2-benzimidazolyl); or ureido or thioureido in which one or more of the hydrogen atoms on the nitrogen atom may be substituted by lower alkyl groups; and pharmaceutically acceptable salts thereof.

6. The anti-HIV composition according to claim 5 wherein the thymidine phosphorylase inhibitor is at least one member selected from the group consisting of 5-chloro-6-(2-iminopyrrolidin-1-yl)methyl-2,4(1H,3H)-pyrimidinedione and pharmaceutically acceptable salts thereof.

7. The anti-HIV composition according to claim 1 comprising trifluridine; at least one member selected from the group consisting of 5-chloro-6-(2-iminopyrrolidin-1-yl)

methyl-2,4(1H,3H)-pyrimidinedione and pharmaceutically acceptable salts thereof; and a pharmaceutically acceptable carrier.

8. The anti-HIV composition according to claim 1 containing 0.05 to 20 moles of the thymidine phosphorylase inhibitor per mole of said at least one member selected from the group consisting of trifluridine and derivatives thereof.

9. The anti-HIV composition according to claim 8 containing 0.1 to 5 moles of the thymidine phosphorylase inhibitor per mole of said at least one member selected from the group consisting of trifluridine and derivatives thereof.

10. A composition for potentiating the anti-HIV activity of trifluridine and derivatives thereof, comprising a thymidine phosphorylase inhibitor and a pharmaceutically acceptable carrier.

11. A method for treating syndromes after HIV infection comprising administering to an HIV infected mammal, including human, an effective amount of an anti-HIV compound which comprises at least one member selected from the group consisting of trifluridine and derivatives thereof.

12. A method for treating syndromes after HIV infection comprising administering an effective amount of the anti-HIV composition of claim 1 to HIV-infected mammals, including humans.

13. A method for treating syndromes after HIV infection comprising administering to an HIV infected mammal, including human, an effective amount of an anti-HIV compound and an anti-HIV activity potentiating compound, wherein the anti-HIV compound comprises at least one member selected from the group consisting of trifluridine and derivatives thereof, and wherein the anti-HIV activity potentiating compound comprises a thymidine phosphorylase inhibitor.

14. The method for treating syndromes after HIV infection of claim 11, wherein the trifluridine derivatives are compounds that can be converted into trifluridine in vivo.

15. The method for treating syndromes after HIV infection of claim 11, wherein the trifluridine and derivatives thereof are compounds of the formula

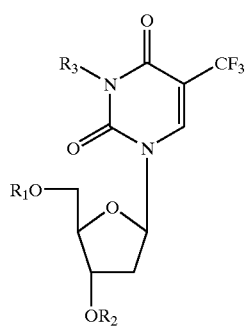

(1)

wherein $R_1$ and $R_2$ may be the same or different and are hydrogen, acyl, lower alkyl, alkoxy-lower alkyl, tetrahydrofuryl, tetrahydropyranyl, triphenylmethy, benzyloxy-lower alkyl, tetrahydrofuryloxy-lower alkyl, lower alkylcarbamoyl, lower alkoxycarbonyl, tri-substituted silyl, di-substituted phosphoric acid group, benzyl or benzoyl;

the three substituents of the tri-substituted silyl and the two substituents of the di-substituted phosphoric acid group may be the same or different from each other and are selected from the group consisting lower alkyl, phenyl and benzyl;

$R_3$ is hydrogen, tetrahydrofliryl or benzoyl;

when $R_1$ or $R_2$ is benzyl, the benzyl may have one or more substituents selected from the group consisting of lower alkyl, lower alkoxy and halogen;

when $R_1$, $R_2$ or $R_3$ is benzoyl, the benzoyl may have one or more substituents selected from the group consisting of lower alkyl, lower alkoxy and halogen.

16. The method for treating syndromes after HIV infection of claim 13, wherein the trifluridine derivatives are compounds that can be converted into trifluridine in vivo.

17. The method for treating syndromes after HIV infection of claim 13, wherein the trifluridine and derivatives thereof are compounds of the formula

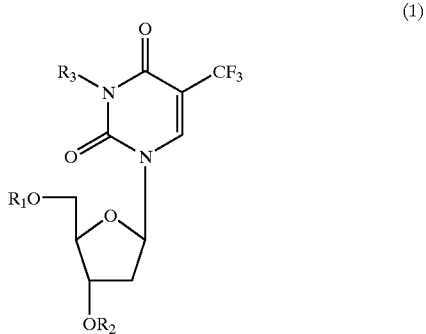

(1)

wherein $R_1$ and $R_2$ may be the same or different and are hydrogen, acyl, lower alkyl, alkoxy-lower alkyl, tetrahydrofuryl, tetrahydropyranyl, triphenylmethy, benzyloxy-lower alkyl, tetrahydrofuryloxy-lower alkyl, lower alkylcarbamoyl, lower alkoxycarbonyl, tri-substituted silyl, di-substituted phosphoric acid group, benzyl or benzoyl;

the three substituents of the tri-substituted silyl and the two substituents of the di-substituted phosphoric acid group may be the same or different from each other and are selected from the group consisting lower alkyl, phenyl and benzyl;

$R_3$ is hydrogen, tetrahydrofuryl or benzoyl;

when $R_1$ or $R_2$ is benzyl, the benzyl may have one or more substituents selected from the group consisting of lower alkyl, lower alkoxy and halogen;

when $R_1$, $R_2$ or $R_3$ is benzoyl, the benzoyl may have one or more substituents selected from the group consisting of lower alkyl, lower alkoxy and halogen.

18. A method for potentiating an anti-HIV activity of trifluridine and derivatives in thereof in a mammal, including human, comprising administering to said mammal, including human, an effective amount of a thymidine phosphorylase inhibitor.

19. A kit for treating syndromes after HIV infection comprising a first composition comprising an anti-HIV compound which comprises at least one member selected from the group consisting of trifluridine and derivatives thereof and a second composition comprising a thymidine phosphorylase inhibitor.

20. The kit for treating syndromes after HIV infection of claim 19, wherein the trifluridine derivatives are compounds that can be converted into trifluridine in vivo.

21. The kit for treating syndromes after HIV infection of claim 19, wherein the trifluridine and derivatives thereof are compounds of the formula

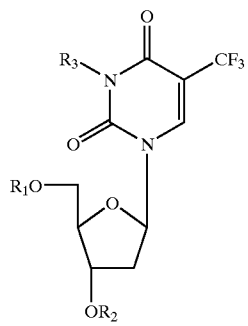

(1)

wherein $R_1$ and $R_2$ may be the same or different and are hydrogen, acyl, lower alkyl, alkoxy-lower alkyl, tetrahydrofuryl, tetrahydropyranyl, triphenylmethy, benzyloxy-lower alkyl, tetrahydrofuryloxy-lower alkyl, lower alkylcarbarnoyl, lower alkoxycarbonyl, tri-substituted silyl, di-substituted phosphoric acid group, benzyl or benzoyl;

the three substituents of the tri-substituted silyl and the two substituents of the di-substituted phosphoric acid group may be the same or different from each other and are selected from the group consisting lower alkyl, phenyl and benzyl;

$R_3$ is hydrogen, tetrahydrofuryl or benzoyl;

when $R_1$ or $R_2$ is benzyl, the benzyl may have one or more substituents selected from the group consisting of lower alkyl, lower alkoxy and halogen;

when $R_1$, $R_2$ or $R_3$ is benzoyl, the benzoyl may have one or more substituents selected from the group consisting of lower alkyl, lower alkoxy and halogen.

* * * * *